United States Patent
Kim et al.

(10) Patent No.: US 11,543,398 B2
(45) Date of Patent: Jan. 3, 2023

(54) CARBONIC ANHYDRASE-CATALYZED ISOTOPE EQUILIBRIUM BETWEEN CO2—H2O FOR OXYGEN ISOTOPE ANALYSES OF AQUEOUS SAMPLES

(71) Applicant: McMaster University, Hamilton (CA)

(72) Inventors: Sang-Tae Kim, Ancaster (CA); Nicolas Randazzo, Stoney Creek (CA); Martin Knyf, Dundas (CA)

(73) Assignee: McMaster University, Hamilton (CA)

( * ) Notice: Subject to any disclaimer, the term of this patent is extended or adjusted under 35 U.S.C. 154(b) by 94 days.

(21) Appl. No.: 16/667,559

(22) Filed: Oct. 29, 2019

(65) Prior Publication Data
US 2020/0132652 A1 Apr. 30, 2020

Related U.S. Application Data

(60) Provisional application No. 62/752,064, filed on Oct. 29, 2018.

(51) Int. Cl.
*G01N 33/18* (2006.01)
*H01J 49/30* (2006.01)

(52) U.S. Cl.
CPC ...... *G01N 33/18* (2013.01); *C12Y 402/01001* (2013.01); *H01J 49/30* (2013.01)

(58) Field of Classification Search
CPC ............. G01N 33/18; G01N 33/182; C12Y 402/01001; H01J 49/30
See application file for complete search history.

(56) References Cited

U.S. PATENT DOCUMENTS

2003/0228708 A1* 12/2003 Huber ............... G01N 1/34 436/181
2013/0062516 A1* 3/2013 Kuo .............. G01N 33/6893 250/282
2014/0322803 A1* 10/2014 Constantz .......... B01D 53/18 435/289.1

OTHER PUBLICATIONS

Uchikawa et al., The effect of carbonic anhydrase on the kinetics and equilibrium of the oxygen isotope exchange in the CO2-H2) system: Implications for d18O vital effects in biogenic carbonates, Geochimica et Cosmochimica Acta 95, (2012), pp. 15-34.
Cohn, Mildred et al., "Oxygen Exchange Reaction of Organic Compounds and Water", Contribution from the Department of Chemistry of Columbia University, Mar. 1938, pp. 679-687.

* cited by examiner

*Primary Examiner* — Jennifer Wecker
*Assistant Examiner* — Kathryn Elizabeth Limbaugh
(74) *Attorney, Agent, or Firm* — Bereskin & Parr LLP/S.E.N.C.R.L., s.r.l.; Sandra Marone

(57) ABSTRACT

The present application relates to a method for improving analytical efficiency and cost effectiveness of oxygen isotope analysis of an aqueous sample. In particular, the present application relates to a method of determining an oxygen isotope composition of an aqueous sample by (a) equilibrating the aqueous sample with $CO_2$ gas wherein the aqueous sample comprises an effective amount of carbonic anhydrase (CA) enzyme; and (b) measuring the oxygen isotope composition of the $CO_2$ at equilibrium, wherein the oxygen isotope composition of the $CO_2$ corresponds to the oxygen isotope composition of the aqueous sample.

18 Claims, 2 Drawing Sheets

Figure 1:
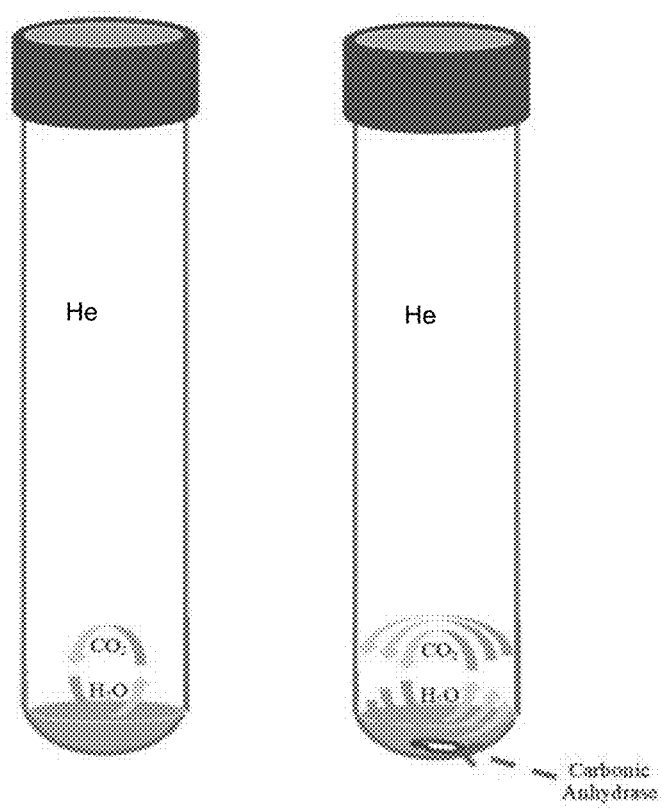

CARBONIC ANHYDRASE-CATALYZED ISOTOPE EQUILIBRIUM BETWEEN CO2—H2O FOR OXYGEN ISOTOPE ANALYSES OF AQUEOUS SAMPLES

CROSS-REFERENCE TO RELATED APPLICATIONS

The present application claims the benefit of priority from U.S. Provisional Patent Application Ser. No. 62/752,064 filed on Oct. 29, 2018, the contents of which are incorporated herein by reference in their entirety.

FIELD

The present application relates to methods used in the field of stable isotope geochemistry and earth sciences which help researchers to determine the oxygen isotope composition of aqueous samples of various origins.

BACKGROUND

Oxygen isotope studies of aqueous samples have been used in many fields of science including, for example, geology, biology, and hydrology and have allowed researchers to better understand environmental or climatic processes on Earth. The classic approach to determine the oxygen isotope composition of water is through the isotopic equilibration of $CO_2$ gas and $H_2O$. Carbon dioxide dissolves in water and exits in chemical equilibrium with carbonic acid, ($CO_2+H_2O \leftrightarrow H_2CO_3$). In the classic approach for determining, the oxygen isotope composition of water, the $CO_2$ gas is injected within a reaction vessel containing the sample water and given time to reach isotopic equilibrium. This time allows the oxygen isotopes within the $CO_2$ gas to reflect the isotopic composition of the water and thereby allow researchers to obtain the oxygen isotope composition of the water being tested. This method is by far the most utilized analytical technique for the oxygen isotope analysis of an aqueous sample, with a typical precision of ≤0.1‰. However, the oxygen isotope exchange between $CO_2$ and $H_2O$ usually takes ~24 hours or longer in a closed and undisturbed reaction vessel at 25° C. Given the widespread use of this "classic $CO_2$—$H_2O$ equilibration method" in stable isotope geochemistry as well as other scientific fields, improving its analytical efficiency and cost effectiveness would have significant implications for the scientific community.

Carbonic anhydrase (CA) is known to catalyze the interconversion of $CO_2$ and $H_2O$ in a $CO_2$ (aqueous)—Water system, (or Dissolved Inorganic Carbon (DIC)-Water system) (see, for example, Uchikawa and Zeebe, Geochmica et Cosmochimica Acta 95, 2012, p 15-34).

SUMMARY

The present application relates to a method of using carbonic anhydrase (CA) to rapidly catalyze the oxygen isotope exchange reaction between $CO_2$ gas and $H_2O$. The present method allows the attainment of oxygen isotope equilibrium at a significantly faster rate than the uncatalyzed reaction. The oxygen isotope equilibrium time observed in the present application is much shorter than what was previously reported and the present enzymatically-catalyzed $CO_2$—$H_2O$ equilibration method represents, to the best of the Applicant's knowledge, the fastest means of establishing oxygen isotope equilibrium between $CO_2$ gas and $H_2O$ known to date. This novel finding is particularly useful since the present CA-catalyzed method is relatively simple, requiring a little more effort than the classic $CO_2$—$H_2O$ equilibration method, and can be directly applied to commercially available $CO_2$—$H_2O$ equilibration devices. Therefore, the present method can be easily and immediately adopted by any laboratory that measures the oxygen isotope composition of aqueous samples.

Accordingly, the present application includes a method of determining an oxygen isotope composition of an aqueous sample comprising:
 (a) equilibrating the aqueous sample with $CO_2$ gas wherein the aqueous sample comprises an effective amount of carbonic anhydrase (CA) enzyme; and
 (b) measuring the oxygen isotope composition of the $CO_2$ at equilibrium,
wherein the oxygen isotope composition of the $CO_2$ corresponds to the oxygen isotope composition of the aqueous sample.

In an embodiment, the method of the present application was able to reduce the time needed for $CO_2$—$H_2O$ equilibration from 24 hours to less than one hour. This is significantly faster than any technique previously disclosed in the literature (including shaking) and greatly improves the efficiency of the well-established technique, essentially saving an entire day of analysis. To the best of the Applicant's knowledge, no previous study has utilized the CA enzyme in this fashion.

Other features and advantages of the present method will become apparent from the following detailed description. It should be understood; however, that the detailed description and the specific examples, while indicating embodiments of the method, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 shows a schematic of the apparatus used in an embodiment of the method of the present application. Water samples and $CO_2$ gas are kept within a reaction vessel in the presence of He gas at a constant temperature for a given time to equilibrate. The classic $CO_2$—$H_2O$ equilibration method requires approximately 24 hours in order to equilibrate $CO_2$ gas with $H_2O$ whereas the newly proposed method which utilizes carbonic anhydrase (CA) requires significantly shorter equilibration time (as indicated by multiple arrows).

Figure 2:
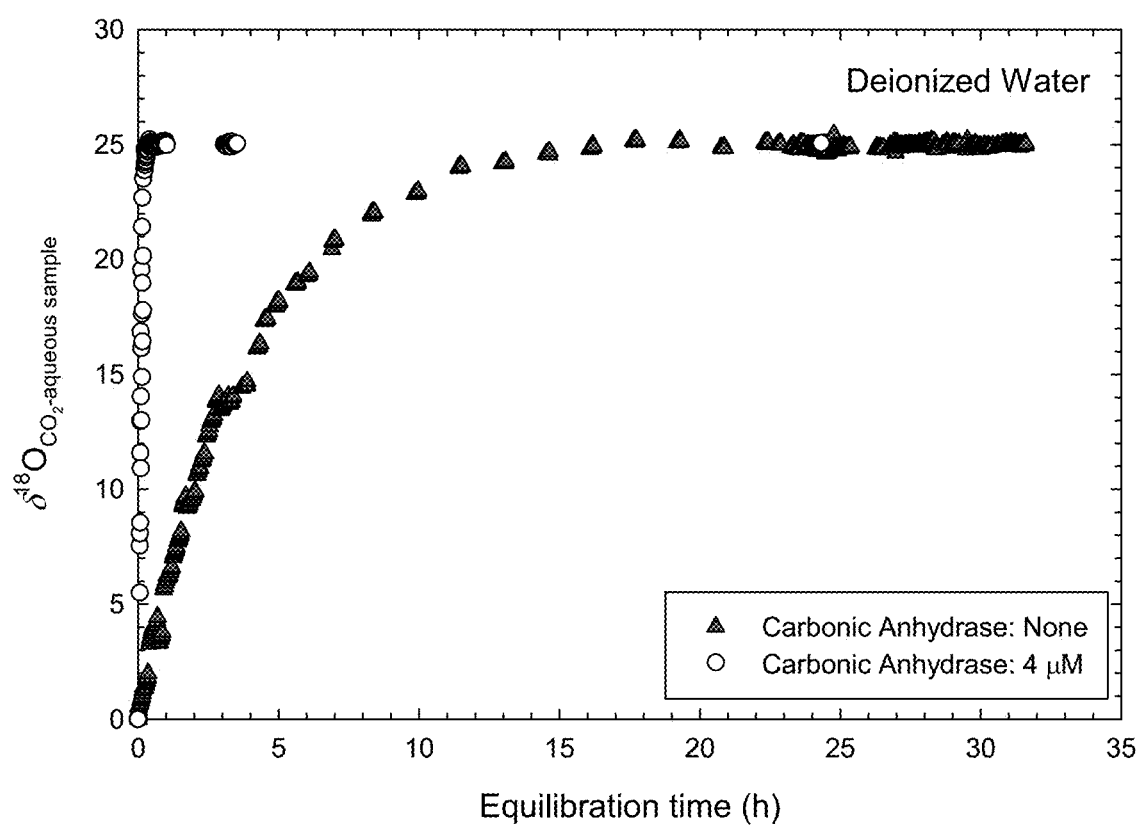

FIG. 2 shows a comparison of the rates of oxygen isotope exchange reaction between $CO_2$ and $H_2O$ for deionized water with (○) and without (▲) CA at 25° C. in an embodiment of the present application. The data without CA (▲) shows the typical equilibration time of the classic $CO_2$—$H_2O$ equilibration method.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

The term "effective amount" as used herein means an amount that is effective and for the periods of time necessary to achieve a desired result. For example, in the context of equilibrating an oxygen isotope composition of an aqueous sample, an effective amount of carbonic anhydrase is an amount that, for example, is effective for achieving oxygen isotope equilibrium between $CO_2$ and $H_2O$.

The term "equilibrium" as used herein refers to a state in a chemical reaction in which rate of the forward reaction equals the rate of the backward reaction such that there is not net change in concentrations of the reactants and products.

DETAILED DESCRIPTION

The classic $CO_2$—$H_2O$ equilibration method is the most popular technique for the measurement of the oxygen isotope composition of aqueous samples in stable isotope geochemistry. It has been now found and reported herein that carbonic anhydrase (CA) enzyme catalyzes the interconversion of $CO_2$ (gas) and $H_2O$ into $H_2CO_3$ (carbonic acid), $HCO_3^-$ (bicarbonate ions), $CO_3^{2-}$ (carbonate ions) and $H^+$. In the present application, a method has been developed that utilizes the carbonic anhydrase (CA) to reduce the $CO_2$—$H_2O$ equilibration time in the classic $CO_2$—$H_2O$ equilibration method. CA is widely present in nature and its use presents a unique opportunity to enhance oxygen isotope exchange kinetics, or oxygen isotope equilibration rate, in the $CO_2$—$H_2O$ system. The Applicants examined whether or not CA could catalyze the oxygen isotope exchange between $CO_2(gas)$ ($CO_{2(g)}$) and $H_2O$ ($\frac{1}{2}C^{16}O_2 + H_2^{18}O \leftrightarrow \frac{1}{2}^{18}O_2 + H_2^{16}O$), and whether or not enzymatically-controlled $CO_2$—$H_2O$ equilibration by carbonic anhydrase (CA) could reduce the time for oxygen isotope equilibrium between $H_2O$ and $CO_2$ at, for example, ambient temperature such as at 25° C. The Applicant has found that CA significantly reduces the oxygen isotope equilibration time and rapidly enhances the efficiency of the classic $CO_2$—$H_2O$ equilibration method.

In an embodiment, the Applicant has found that the method of the present application was able to reduce the time needed for $CO_{2(g)}$—$H_2O$ equilibration from 24 hours to less than one hour. This is significantly faster than any known method previously disclosed in the literature (including shaking) and greatly improves the efficiency of the well-established method, essentially saving an entire day of analysis. To the best of the Applicant's knowledge, no previous study is known to utilize the CA enzyme in this fashion.

Accordingly, the present application includes a method for improving analytical efficiency and cost effectiveness of oxygen isotope analysis of an aqueous sample, comprising: the use of carbonic anhydrase (CA) enzyme. The present application further includes a use of carbonic anhydrase (CA) enzyme for improving analytical efficiency and cost effectiveness of oxygen isotope analysis of an aqueous sample.

The present application also includes a method of determining an oxygen isotope composition of an aqueous sample comprising:
  (a) equilibrating the aqueous sample with $CO_2$ gas wherein the aqueous sample comprises an effective amount of carbonic anhydrase (CA) enzyme; and
  (b) measuring the oxygen isotope composition of the $CO_2$ at equilibrium,
wherein the oxygen isotope composition of the $CO_2$ corresponds to the oxygen isotope composition of the aqueous sample.

It would be appreciated by a person of skill in the art that different aqueous samples may have varying isotopic compositions. In an embodiment, the aqueous sample is deionized water, freshwater, seawater, or brine. In an embodiment, the aqueous sample is seawater. In an embodiment, the seawater is artificial seawater or desalinized deep seawater. In an embodiment, the aqueous sample is freshwater. In an embodiment, the freshwater is iceberg water.

In an embodiment, the effective amount of carbonic anhydrase (CA) enzyme is about 2 μmolal and above. In an embodiment, the effective amount of carbonic anhydrase (CA) enzyme is about 4 μmolal and above. In an embodiment, the effective amount of carbonic anhydrase (CA) enzyme is about 2 μmolal to about 10 μmolal. In an embodiment, the effective amount of carbonic anhydrase (CA) enzyme is about 4 μmolal to about 10 μmolal. In an embodiment, the effective amount of carbonic anhydrase (CA) enzyme is about 4 μmolal to about 8 μmolal. In an embodiment, the effective amount of carbonic anhydrase (CA) enzyme is about 4 μmolal.

In an embodiment, measuring the oxygen isotope composition is performed using a mass spectrometer. In an embodiment, the mass spectrometer is a stable isotope ratio mass spectrometer. In an embodiment, the mass spectrometer is a continuous flow isotope ratio mass spectrometer (CF-IRMS).

In an embodiment, the isotopic equilibrating occurs in less than about one hour. In an embodiment, the equilibrating occurs in less than about 50 minutes. In an embodiment, the equilibrating occurs in less than about 30 minutes. In an embodiment, the equilibrating occurs in less than about 20 minutes. In an embodiment, the equilibrating occurs in about 20 minutes or less.

In an embodiment, the equilibrating is performed at ambient temperature. In an embodiment, the equilibrating is performed at about 15° C. to about 30° C. In an embodiment, the equilibrating is performed at about 25° C.

In an embodiment, the oxygen isotope composition of the $CO_2$ at equilibrium of the aqueous sample comprising an effective amount of carbonic anhydrase (CA) enzyme is substantially the same as the oxygen isotope composition of the $CO_2$ at equilibrium of an aqueous without CA.

The present application also includes a use of carbonic anhydrase (CA) for determining an oxygen isotope composition of an aqueous sample.

The present application further includes a kit for determining an oxygen isotope composition of an aqueous sample, the kit comprising carbonic anhydrase and instructions for determining the oxygen isotope composition of the aqueous sample, for example, using a method of the present application.

The following non-limiting examples are illustrative of the present application.

Examples

FIG. 1 shows a schematic of the apparatus used in an embodiment of the present method. Water samples and $CO_2$ gas are kept within a reaction vessel in the presence of He gas at a constant temperature for a given time to isotopically equilibrate.

A series of $CO_2$ gases were equilibrated with four types of aqueous samples (i.e., deionized water, artificial seawater, desalinized deep seawater, and iceberg water) containing CA using a continuous flow isotope ratio mass spectrometer (CF-IRMS) equipped with an automated gas sample collection device. To optimize experimental protocols, the effect of CA concentration in an aqueous sample, the influence of drying technique (i.e., drying with nitrogen gas and freeze drying) for the preparation of sample vials containing dried CA, the age of CA stock solution, and the ionic strength and the oxygen isotope composition of aqueous samples were examined. All of the tested elements at ~4 μmolal CA concentration did not influence the results of the isotopic analysis with CA.

FIG. 2 shows an example of the present method rapidly accelerating the time required for $CO_2$—$H_2O$ equilibration compared to when CA is not present. A concentration of ~4 μmolal CA was used. Additional analyses found that this method works for seawater as well as different types of waters of varying isotopic composition, thus this technique can be used on a wide range of different waters and maintain its viability.

With reference to FIG. 2, the oxygen isotope equilibration (via change in $\delta^{18}O_{CO2\text{-}aqueous\ sample}$) between $CO_2$ gas and both deionized water with and without the presence of CA can be seen. The oxygen isotope composition of the $CO_2$ gas that was equilibrated with deionized water samples (or $\delta^{18}O_{CO2\text{-}deionized}$ water sample) prepared with ~4 μmolal CA began at 0‰, but increased surprisingly fast until stabilizing at 25.00±0.09‰ in ~0.3 hours, representing a significantly faster rate of oxygen isotope exchange between $CO_2$ gas and water, compared to the rate of oxygen isotope exchange between $CO_2$ gas and water without CA. The oxygen isotope composition of the $CO_2$ gas at isotopic equilibrium with deionized water without CA was 24.96±0.10‰ and the oxygen isotope equilibrium was established after ~19 hours. Furthermore, the equilibrium oxygen isotope composition for deionized water were statistically identical regardless of the presence or absence of CA and thus no data correction procedure is required, up to ~4 μmolal CA, to account for the concentration effect of CA when the oxygen isotope composition is reported.

Therefore, the Applicants have found that aqueous samples containing, for example, 4 μmolal of CA significantly enhances $CO_2$—$H_2O$ equilibration kinetics compared to samples with no CA, with the $CO_2$—$H_2O$ equilibration time of deionized water and artificial seawater (ionic strength=~0.6) being reduced from 19 hours and 23 hours to ~0.3 hours (20 minutes) and ~0.77 hours (47 minutes), respectively at 25° C. The two drying techniques (drying with nitrogen gas or freeze drying) employed and ageing the stock solutions up to 4 weeks did not affect CA's enzymatic activity. Accordingly, CA can be used to rapidly catalyze the oxygen isotope exchange between $CO_2$ and $H_2O$, and significantly reduce the equilibration time of the classic $CO_2$—$H_2O$ equilibration method.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

The invention claimed is:

1. A method of determining an oxygen isotope composition of an aqueous sample comprising:
    (a) equilibrating the aqueous sample with $CO_2$ gas in a vessel, wherein the aqueous sample comprises an effective amount of carbonic anhydrase (CA) enzyme and the $CO_2$ gas is located in a space in contact with and adjacent to the aqueous sample in the vessel; and
    (b) measuring the oxygen isotope composition of the $CO_2$ gas at equilibrium by sampling the $CO_2$ gas from the space in the vessel,
wherein the oxygen isotope composition of the $CO_2$ gas corresponds to the oxygen isotope composition of the aqueous sample and the effective amount of the CA enzyme is an amount that catalyzes the equilibrium of $CO_2$ gas and $H_2O$.

2. The method of claim 1, wherein the aqueous sample is deionized water, freshwater, seawater, or brine.

3. The method of claim 2, wherein the aqueous sample is seawater.

4. The method of claim 3, wherein the seawater is artificial seawater or desalinized deep seawater.

5. The method of claim 2, wherein the aqueous sample is freshwater.

6. The method of claim 5, wherein the freshwater is iceberg water.

7. The method of claim 1, wherein the effective amount of carbonic anhydrase (CA) enzyme is about 2 μmolal to about 10 μmolal.

8. The method of claim 1, wherein the effective amount of carbonic anhydrase (CA) enzyme is about 4 μmolal.

9. The method of claim 1, wherein measuring the oxygen isotope composition is performed using a mass spectrometer.

10. The method of claim 9, wherein, the mass spectrometer is a stable isotope ratio mass spectrometer.

11. The method of claim 9, wherein the mass spectrometer is a continuous flow isotope ratio mass spectrometer (CF-IRMS).

12. The method of claim 1, wherein the equilibrating occurs in less than about one hour.

13. The method of claim 1, wherein the equilibrating occurs in about 20 minutes.

14. The method of claim 1, wherein the equilibrating is performed at ambient temperature.

15. The method of claim 14, wherein the ambient temperature is about 25° C.

16. The method of claim 1, wherein the oxygen isotope composition of the $CO_2$ gas at equilibrium of the aqueous sample comprising an effective amount of carbonic anhydrase (CA) enzyme is substantially the same as the oxygen isotope composition of the $CO_2$ gas at equilibrium of an aqueous sample without CA.

17. A kit for determining an oxygen isotope composition of an aqueous sample, the kit comprising carbonic anhydrase and instructions for determining the oxygen isotope composition of the aqueous sample using the method of claim 1.

18. The method of claim 1, wherein the effective amount of carbonic anhydrase (CA) enzyme is greater than about 2 µmolal.

* * * * *